(12) United States Patent
Miziolek et al.

(10) Patent No.: US 8,248,602 B2
(45) Date of Patent: Aug. 21, 2012

(54) LASER ASSISTED MICROWAVE PLASMA SPECTROSCOPY

(76) Inventors: Andrzej Miziolek, Lutherville, MD (US); Philip C. Efthimion, Bedminster, NJ (US)

( * ) Notice: Subject to any disclaimer, the term of this patent is extended or adjusted under 35 U.S.C. 154(b) by 0 days.

(21) Appl. No.: 13/084,211

(22) Filed: Apr. 11, 2011

(65) Prior Publication Data

US 2012/0008139 A1    Jan. 12, 2012

Related U.S. Application Data

(63) Continuation of application No. 12/446,321, filed as application No. PCT/US2007/081730 on Oct. 18, 2007, now abandoned.

(60) Provisional application No. 60/829,899, filed on Oct. 18, 2006.

(51) Int. Cl.
*G01J 3/30* (2006.01)
(52) U.S. Cl. ........................................ 356/318
(58) Field of Classification Search .................. 356/318
See application file for complete search history.

(56) References Cited

U.S. PATENT DOCUMENTS

| | | | |
|---|---|---|---|
| 5,379,103 A | 1/1995 | Zigler | |
| 5,847,825 A | 12/1998 | Alexander | |
| 6,008,897 A | 12/1999 | Sabsabi et al. | |
| 6,532,068 B2 * | 3/2003 | Detalle et al. | 356/318 |
| 6,661,511 B2 | 12/2003 | Detalle et al. | |
| 2007/0076200 A1 * | 4/2007 | Martin et al. | 356/318 |

FOREIGN PATENT DOCUMENTS

JP   2003-35671   * 2/2003

* cited by examiner

*Primary Examiner* — Kara E Geisel
(74) *Attorney, Agent, or Firm* — Fox Rothschild LLP; Richard C. Woodbridge; Ryan Miller

(57) ABSTRACT

The present invention has a laser and a second energy source act in combination to produce a plasma that emits characteristic radiation for a prolonged period of time. The laser energy is directed to a sample for a period of time to ignite a plasma containing the sample material and to either ablate or vaporize the sample. Energy from a second energy source is supplied to the plasma for a second period of time so that the characteristic radiation emitted by the plasma is maintained. The emitted radiation is used to identify chemical elements contained in the sample. The second period of time is typically larger than the first period of time and may be as long as many milliseconds. Supplying energy for this longer period of time allows the plasma to grow in size and contributes to the large enhancement in the detection sensitivity of the present invention.

23 Claims, 7 Drawing Sheets

28: Direct laser energy to a sample material for a first period of time to ignite a plasma 30: Supply energy from a second energy source to the plasma for a second period of time, typically longer than the first period of time 32: Detect radiation emitted by the plasma 28: Direct laser energy to a sample material for a first period of time to ignite a plasma 30: Supply energy from a second energy source to the plasma for a second period of time, typically longer than the first period of time 32: Detect radiation emitted by the plasma

LASER ASSISTED MICROWAVE PLASMA SPECTROSCOPY

CROSS REFERENCE TO APPLICATIONS

This application is a Continuation of U.S. patent application Ser. No. 12/446,321 filed Apr. 20, 2009, which is a 371 National Phase Application of PCT Application No. PCT/US2007/081730 filed on Oct. 18, 2006, which in turn claims priority of U.S. Provisional Patent Application Ser. No. 60/829,899 filed on Oct. 18, 2006, entitled "Long Pulse Plasma Heating to Enhance Laser-Induced Plasma Spectroscopy", the contents of which are hereby incorporated by reference.

TECHNICAL FIELD

The present invention relates to the production of plasmas for spectroscopy, and more particularly to the use of a combination of a laser and a second energy source to produce a plasma that emits characteristic radiation for a prolonged period of time.

BACKGROUND ART

Analytical techniques to measure chemical, biological, and explosive agents typically require samples to be taken and brought to a laboratory for analysis. Since 9/11, however, military and homeland security requirements have developed a critical need to detect explosives, and biological and chemical warfare agents, rapidly and in-situ.

One technique developed in response to this need is Laser Induced Breakdown Spectroscopy (LIBS). LIBS can be used to measure trace element concentrations in solids, liquids and gases, with spatial resolution and absolute quantification being feasible, down to parts-per-million concentration levels. LIBS operates by analyzing the spectral emission from laser-induced micro plasmas. A laser is used to ablate some material from a surface, or to vaporize air borne material. At the same time, the laser is focused to a sufficiently small beam size to create a small plasma of the ablated or vaporized material. In LIBS, laser energies on the order of 20-200 mJ are typically used to create plasmas that are typically on the order of 1-5 mm in size. The light spectrum from the plasma spark is then used to identify trace elements in the sample. This is typically accomplished by coupling the light to a spectrometer or a series of light detectors with optical filters. The spectral information may then be used to analyze the sample.

LIBS has the advantages of being a simple, rapid, real-time analytical technique that does not require any sample preparation. LIBS, therefore, has potential applications to Homeland Security and Military Security because it can detect explosives, biological, and chemical agents.

LIBS, however, has some serious limitations. Because of the small size and short lifetime of the LIBS micro plasma, the minimum detection limit is only in the range of parts per million, in many cases. Detection is even less sensitive if the sample is located any appreciable distance away. Furthermore, because there is minimal light created with this technique, high energy lasers have to be used that tend to damage the surfaces from which the samples are taken. With these high laser energies, there are also concerns about eye safety.

LIBS is described in, for instance U.S. Pat. No. 5,379,014 issued to Zigler on Jan. 3, 1995 entitled "Method and apparatus for in situ detection of minute amounts of trace elements" and U.S. Pat. No. 5,847,825 issued to Alexander on Dec. 8, 1998 entitled "Apparatus and method for detection and concentration measurement of trace metals using laser induced breakdown spectroscopy", the contents of both of which are hereby incorporated by reference.

Various attempts have been made to overcome the limitations of LIBS including attempts to use multiple laser pulses as described in, for instance, U.S. Pat. No. 6,008,897 issued to Sabsabi, et al. on Dec. 28, 1999 entitled "Method and apparatus for materials analysis by enhanced laser induced plasma spectroscopy" and U.S. Pat. No. 6,661,511 issued to Detalle, et al. on Dec. 9, 2003 entitled "Method and apparatus for enhanced laser-induced plasma spectroscopy using mixed-wavelength laser pulses", the contents of both of which are hereby incorporated by reference. None of the attempts at enhancement appear to make more than a factor of 40 enhancement in the sensitivity of LIBS.

To make LIBS a truly useful method requires a sensitivity enhancement of at least a factor of 100, and preferably by a factor of 1000.

DISCLOSURE OF INVENTION

The present invention relates to the production of plasmas for spectroscopy.

In a preferred embodiment, the present invention uses a laser and a second energy source acting in combination to produce a plasma that emits characteristic radiation for a prolonged period of time.

In particular, laser energy is directed to a sample material for a period of time so that it ignites a plasma containing the sample material. Energy from a second energy source is supplied to the plasma for a second period of time so that the radiation emitted by the plasma is maintained. The radiation emitted from the plasma is detected.

The laser energy directed to the sample material may ablate or vaporize the sample material.

The radiation emission maintained by the second energy source is the characteristic radiation that is indicative of an atomic composition of one or more elements in the sample material. Using this radiation, one or more chemical elements or compounds contained in the sample material may be identified. The second period of time is typically larger than the first period of time and may be as long as many milliseconds. Supplying energy for this longer period of time allows the plasma to grow in size and contributes to the large enhancement in the detection sensitivity of the present invention.

These and other features of the invention will be more fully understood by references to the following drawings.

BEST MODE FOR CARRYING OUT THE INVENTION

Figures 1, 2:
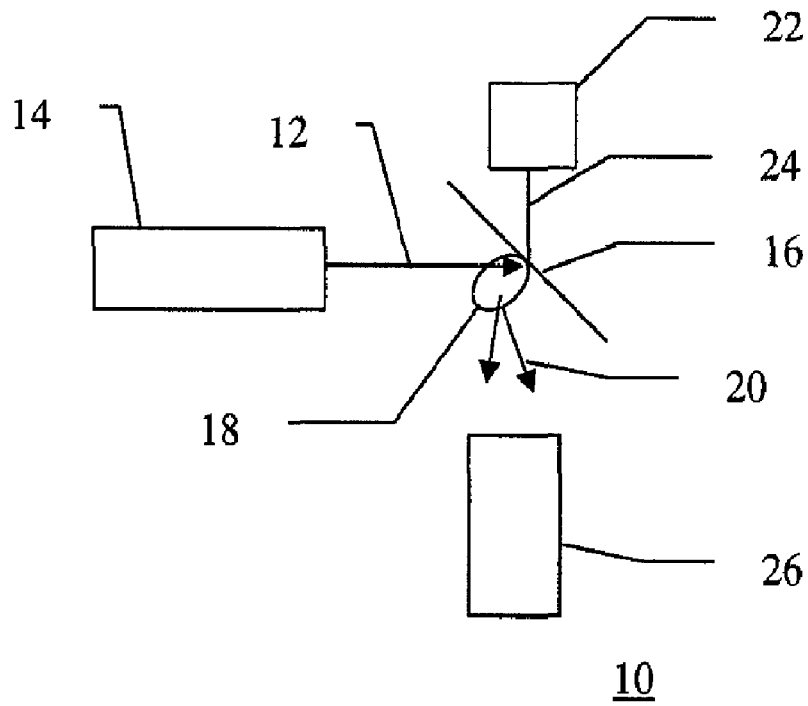
FIG. 1 is a schematic diagram of a laser assisted microwave plasma spectroscopy system.
FIG. 2 is a flow chart showing relevant steps of a laser assisted microwave plasma spectroscopy method.

The present invention relates to a system and method for the production of plasmas for spectroscopy. In particular, the present invention relates to the use of a combination of a laser and a second energy source to produce a plasma that emits characteristic radiation for a prolonged period of time. In this way, a method of spectroscopy that improves on the sensitivity of Laser Induced Breakdown Spectroscopy (LIBS) by a factor of 100 to 1000 may be produced.

In one embodiment of the present invention, termed Laser Assisted Microwave Plasma Spectroscopy (LAMPS), a laser is used to ablate, or vaporize, sample material and to ignite a plasma containing the sample material. Microwave energy is then supplied to the plasma to grow the plasma by the Townsend Effect and to sustain the plasma at a sufficiently high temperature that the plasma continues to emit radiation. By controlling the amount of microwave power and the pulse length of the microwaves, they may be preferentially absorbed by the excited electrons from the material of interest and not be wasted on other species not of interest that may also be in the plasma.

In a preferred embodiment, the microwave pulse length is continued as long as the ablated material or excited gases are in the microwave plasma region. Most materials studied have benefited from microwave pulse lengths up to 4 milliseconds for plasma of size of a few centimeters. Consequently, all of the ablated or vaporized material radiates until it leaves the microwave plasma region. This region can be centimeters to 10's of centimeters in dimension. This technique is optimized by matching the expansion of the excited material of interest and the growth of the microwave plasma region to maximize the radiation from the material of interest, minimize radiation from non-interesting species and minimize the microwave power.

In the present invention a laser is used to ablate or vaporize and excite material from a surface or in a gas and the pre-selected material is formed into atmospheric microwave plasma. The invention includes optimizing the radiation from the material of interest by growing the microwave plasma size using the Townsend Effect to match the expansion of the laser excited material and then the plasma is sustained as long as the ablated material remains in the plasma region. Measurements have shown this to be less than 4 milliseconds in small desk top plasmas where they extend 1 cm from the ablation surface. The other part of the optimization process is to minimize the microwave power so the emission spectrum is dominated by the ablated material or selected gas and not by the surrounding atmosphere. With minimal power, the microwaves lock onto and are absorbed by the ablated and vaporized material. The optimization process provides the largest enhancement over the LIBS process. Enhancements of 100-1000 are achievable.

The technique was demonstrated in a series of lab tests to detect explosive, and chemicals agents with sensitivity of a factor of 100-1000 greater than the LIBS technique and has the potential to have measurement sensitivity in the range of parts per billion. When measurements are conducted on a desktop the microwave fields are confined in a cavity or just outside a hole in a microwave cavity. The laser ablates material from a surface or excites gas near a hole in the cavity or directly inside the cavity. When the material is inside the cavity, the initial LIBS plasma produced by the laser then grows by the Townsend Effect using the microwave power inside the cavity. For the case of the sample material outside a hole in the cavity, some of the microwave field emanates from the cavity hole and the plasma initially grows starts outside the cavity but quickly pass through the hole and the growth continues inside the cavity. For either case the expansion of the excited material matches the growth of the plasma to optimize the spectroscopic light from the ablated material. Typical microwave power levels are 0.1-10 kW. If the microwaves are ON for 1-5 milliseconds or more, the signals can be 100-1000 times more sensitive than LIBS. Microwave frequencies of 0.1-300 GHz can be used for the LAMPS technique. Because the laser in the LAMPS technique is not used to produce the light emission necessary for the analysis, the smallest amount of laser energy is required (1 micro Joule-50 milli Joules) to provide the ablation and excite the ablated material. Consequently, the LAMPS technique creates minimum surface damage compared to the high laser energy density technique of LIBS.

The LAMPS technique can be employed to make measurements at distances of 1-1000 meters by beaming the microwaves with a large antenna to a small spot where the laser selects material to ablate or vaporize and excite, and the microwaves couple to the material. In this case the LAMPS technique can be a factor of 1000 more sensitive than LIBS because the LIBS plasma is far smaller than the larger microwave plasma at far distances. These long distance measurements can be made from a large jeep-like vehicle, a plane, a ship, or from a stationary position. The microwave frequency used in LAMPS is in the range of 0.1-20 GHz for bench top measurements and is in the range of 10-300 GHz for long distance measurements. Laser light can be at a wavelength in the range of 10 microns to 100 nanometers to preferentially pre-select material to ablate. LAMPS has applications in Homeland and Military Security to detect explosives, chemicals, and biological agents.

Alternately, the microwaves can be replaced by a long pulse laser, such as a $CO_2$ laser. Laser wavelengths of 10 microm-194 nm can be considered for this application. Furthermore, a pulsed DC electric field can create the plasma instead of a second laser or microwave power. Normally, LIBS sensitivity is on the order of 1 part per million. However, the sensitivity of the LAMPS process with this enhancement factor can approach the range of parts per billion. To ablate material from a surface and create small micro plasma, the laser in the LIBS technique supplies a power flux in excess of 2 GW/cm2. Alternately, to sustain the LAMPS plasma only requires 250 W/cm$^2$. This is readily achieved with a power up to 5000 Watts . Consequently, a relatively modest level of external power compared to the peak LIBS laser power is required for sensitive measurements. Furthermore, the extremely high laser power densities in LIBS measurements are known to damage sample surfaces.

A preferred embodiment of the invention will now be described in detail by reference to the accompanying drawings in which, as far as possible, like elements are designated by like numbers.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

FIG. 1 is a schematic diagram of a laser assisted microwave plasma spectroscopy system 10. Laser energy 12, from a laser 14, is directed to a sample material 16 for a first period of time. The directed laser energy 12 ignites a plasma 18 containing the sample material 16. The plasma 18 emits radiation 20. A second energy source 22 supplies energy 24 to the plasma 18 for a second period of time. The energy 24 supplied by the second energy source 22 maintains emission of the radiation 20 from the plasma 18. A detector 26 detects the radiation 20 emitted by the plasma 18.

The second period of time is typically longer than the first period of time. The increased length of time may be a factor of two, of four, of fifty, or a hundred or even longer. The increased sensitivity of the LAMPS technology is related to the increased length of time the plasma is kept heated by the second pulse and may be proportional to the increased time.

Obtaining a microwave power supply that provides exact controllable power for a period of time of a few milliseconds to a few second requires specific design, as conventional radar microwaves are only used for very short, microsecond pulses. Commercial and consumer microwave ovens supply unregulated continuous power that is really a 50 hertz pulsed supply.

FIG. 2 is a flow chart showing relevant steps of the laser assisted microwave plasma spectroscopy 10 method.

In step 28, laser energy is directed to a sample material to ignite a plasma.

In step 30, energy is supplied to the plasma from a second energy source.

In step 32, radiation emitted from the plasma is detected.

Figure 3A:
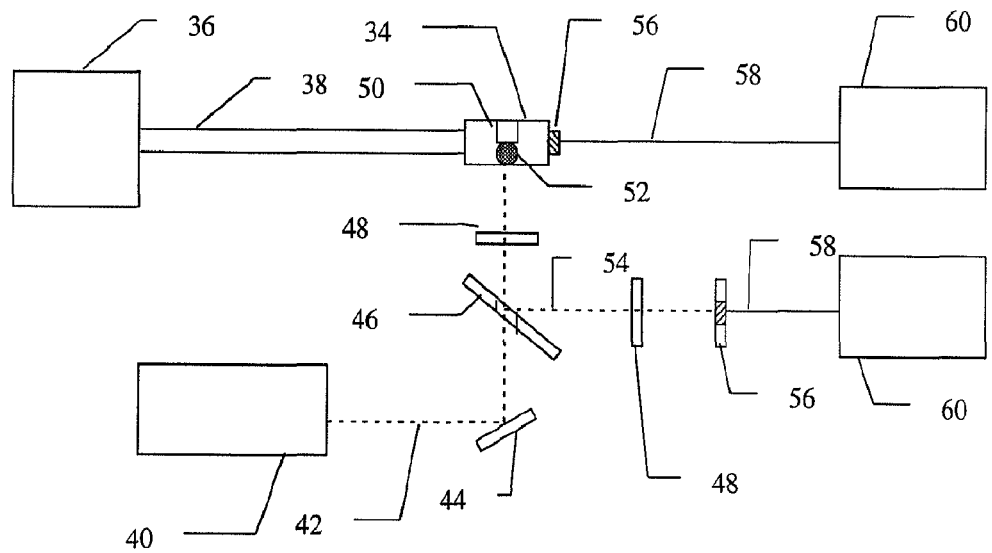
FIG. 3A is a diagram of the experimental configuration including the layout of the optical system and the microwave cavity/target chamber.

FIG. 3A is a diagram of the experimental configuration including the layout of the optical system and the microwave cavity/target chamber.

FIG. 3A is representative of laboratory desktop experiments conducted to demonstrate the greater signals produced by LAMPS over LIBS. Microwaves are confined in a microwave cavity 34 that also functions as the sample target chamber. In a preferred embodiment, the frequency of a microwave generator 36 is 2.45 GHz. A metal waveguide 38 transports the microwave power into the microwave cavity 10. An ablation laser 40 generates laser light 42. The ablation laser 40 is typically a Neodymium, YAG or UV laser. The laser light 42 reflects off a mirror 44 and passes through a hole in a large mirror 46 and is focused with a lens 48 into the microwave cavity 34, where a sample 50 to be analyzed is mounted. When the ablation laser 40 is fired, the laser light 42 ablates material to be analyzed from the sample 50, and also creates a plasma 52 in the microwave cavity 10. Light 54 from the plasma 52 is collected by the large mirror 46 and is then focused with the lens 48 onto an optical fiber 58 that is held in place with a fiber mount 56. The optical fiber 58 transports the light 54 of the plasma 52 to a spectrometer 60 to analyze the plasma light 30.

In alternative embodiment, the optical fiber 58 and the fiber mount 56 may be attached directly to the microwave cavity 34.

The microwave pulse is synchronized to the firing of the ablation laser 40. The range of useable microwave frequencies is 0.1-300 GHz. The range of useable microwave power is on the order of 0.1-10 kW.

The ablation laser 40 may, for instance, be a Big Sky Ultra™ ND:YAG laser as supplied by Big Sky Laser, Inc., of Bozeman, Montana or UV laser such as the Tempest™ UV laser supplied by New Wave, Inc. of Freemont, Calif.

The micro-wave generator 36 may, for instance, be a Toshiba model E3394K microwave tube supplied by Toshiba America, Inc. of New York, N.Y.

Figure 3B:
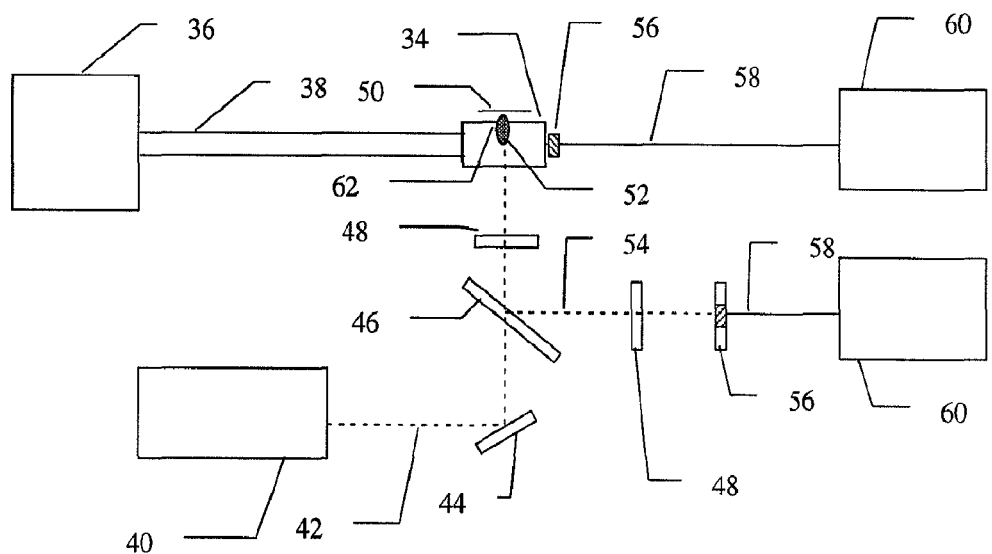
FIG. 3B is a diagram of the experimental configuration including the layout of the optical system and the microwave cavity with the target outside the cavity.

FIG. 3B is a diagram of the experimental configuration including the layout of the optical system and the microwave cavity with the target outside the cavity.

In this embodiment of the invention, the sample 50 is situated outside the microwave cavity 34 and sits a few millimeters away, near a hole in the microwave cavity 34. The frequency of the microwave generator 36 is 2.45 GHz and the metal waveguide 38 transports the microwave power into the microwave cavity 34. The ablation laser 40 generates laser light 42. The laser light 42 reflects off the mirror 44 and passes through a hole in the large mirror 46 and is focused with the lens 48 through the microwave cavity 34 onto the sample 50 mounted outside the microwave cavity 34. When the ablation laser 40 is fired, the laser light 42 ablates sample material to be analyzed from the sample 50, and also creates the plasma 52 outside the microwave cavity 34. The plasma 52 starts on the sample 50 and grows through a hole 62 in the microwave cavity 34. The light 54 from the plasma 52 is collected by the large mirror 46 and is then focused with the lens 48 onto the optical fiber 58 that is held in place with the fiber mount 56. The optical fiber 58 transports the light 54 of the plasma 52 to a spectrometer 60 to analyze the light 54. There may also, or instead be an optical fiber 58 viewing the plasma 52 from the side and with its fiber mount 56 attached directly to the microwave cavity 34. The microwave pulse from the microwave generator 36 is synchronized to the firing of the ablation laser 40. The range of useable microwave frequencies is 0.1-300 GHz. The range of useable microwave power is on the order of 0.1-10 kW.

The light 54 is characteristic radiation, i.e., radiation that is characteristic of an atomic composition of one more elements in the sample. The characteristic radiation can be used to identify the elements using the well-known techniques of spectroscopy.

Figure 4:
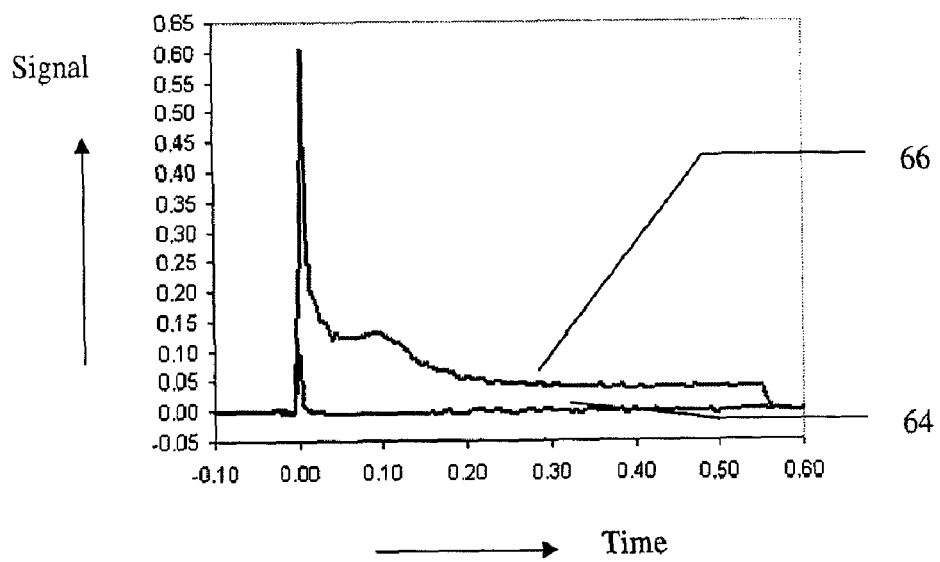
FIG. 4 is a comparison of the time traces of an aluminum spectral line emission created with the standard LIBS technique and the LAMPS technique.

FIG. 4 is a comparison of the time traces of an aluminum spectral line emission created with the standard LIBS technique and the LAMPS technique. In particular, a time trace of an aluminum spectral line emission created by a standard LIBS technique 64 is compared with a time trace of an aluminum spectral line emission created with the LAMPS technique 66. As can be seen, the observed signal from the LAMPS technique is as high as 500 greater than the standard LIBS technique. This enhancement is achieved because in the LAMPS technique, the plasma is sustained for 1.2 milliseconds (1,200 microseconds). Based on these observations, enhancements exceeding 1000 are realistic.

Figure 5:
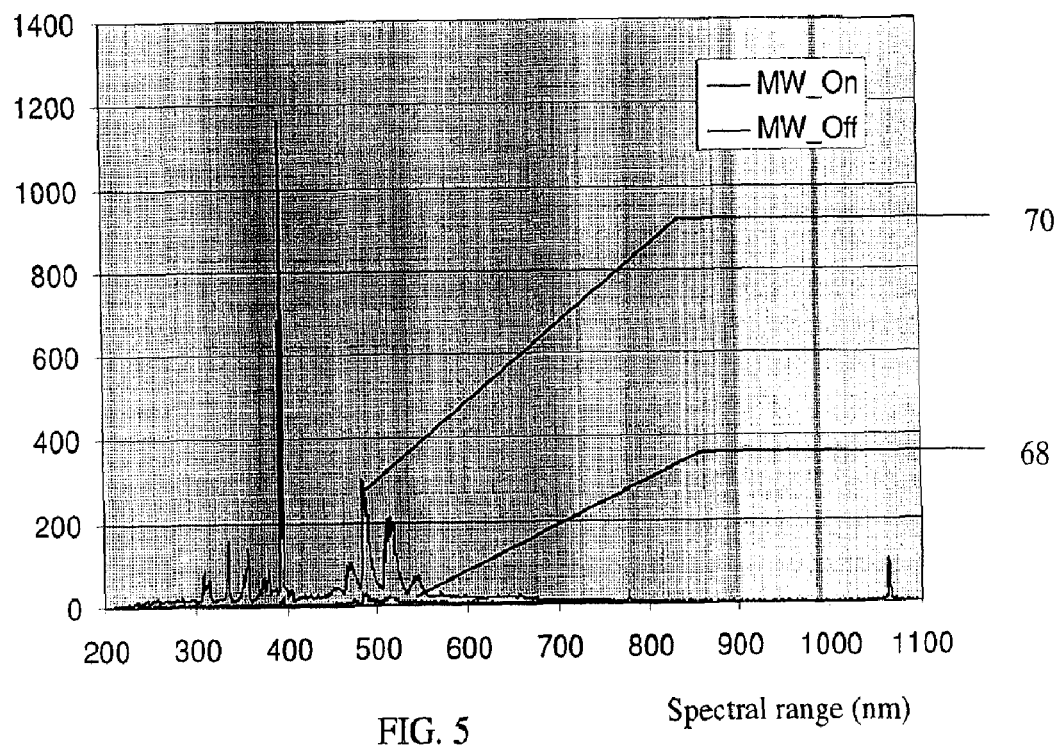
FIG. 5 is a comparison of aluminum spectra at low laser energy with and without microwave energy.

FIG. 5 is a comparison of aluminum spectra at low laser energy with and without microwave energy. FIG. 5 compares a time integrated aluminum spectra measured by LIBS 68 with a time integrated aluminum spectra measured by LAMPS 70. The 394 nm aluminum line shows a factor of 100 greater photon counts by the LAMPS technique. The increase in sensitivity was achieved by sustaining the plasma for the duration of time the selected material was in the plasma and matching the growth of the plasma by the Townsend Effect to the expansion of the excited material. In this case only 7 mJ of laser energy was used to ablate the aluminum and initiate the microwave plasma.

Figure 6:
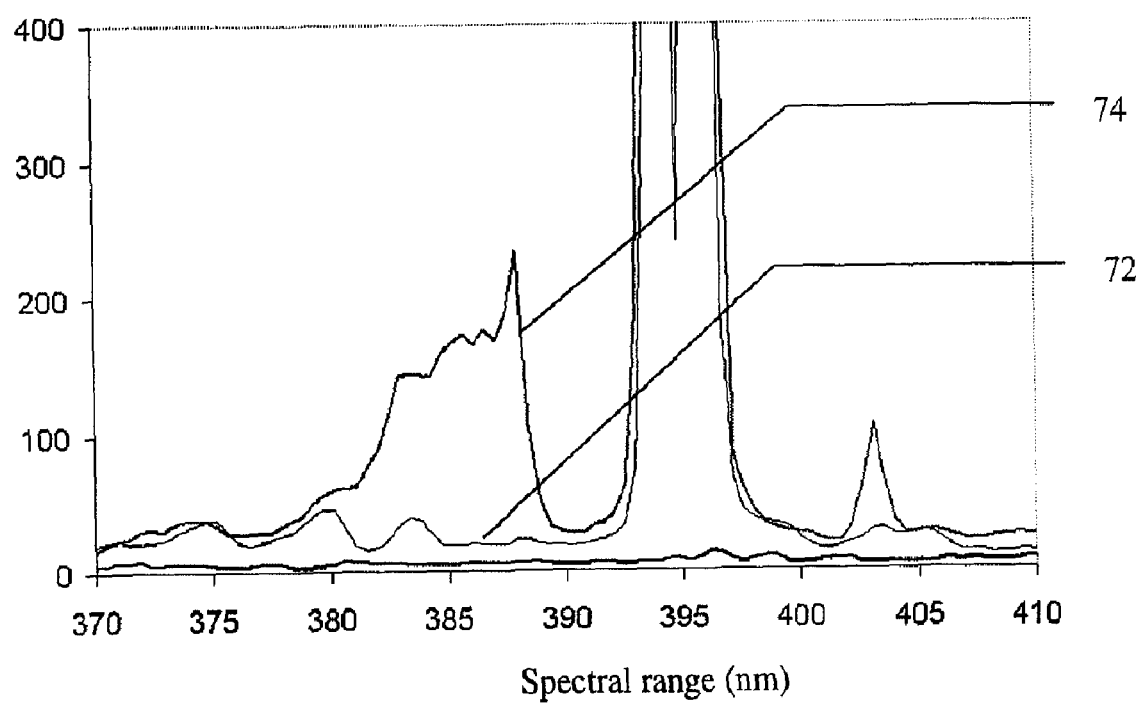
FIG. 6 is a comparison of DNT on an aluminum substrate for LAMPS and LIBS in the narrow spectral range near 385 nm.

FIG. 6 is a comparison of DNT on an aluminum substrate for LAMPS and LIBS in the narrow spectral range near 385 nm. In particular, FIG. 6 shows a LIBS spectrum of the explosive surrogate DNT 72 compared with a LAMPS spectrum of the explosive surrogate DNT 74. The spectrum has a radical feature in the 380-390 nm spectral range that is CN. This spectral feature for the LAMPS technique 74 is 500 times greater than the measurement with the LIES technique 72.

Figure 7A:
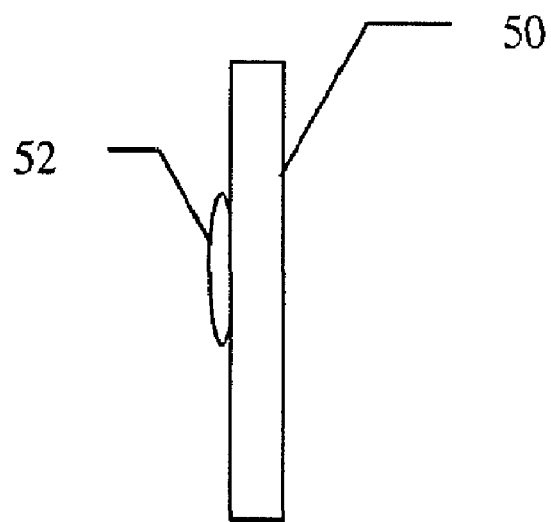
FIG. 7A is a schematic representation of an optical image of an aluminum line radiation light at 30 mJ laser energy for the LIBS technique.

FIG. 7A is a schematic representation of an optical image of an aluminum line radiation light at 30 mJ laser energy for the LIBS technique. An aluminum sample 50 was examined with the LIES laser focused on the sample. The image of the plasma 52 was measured by a digital camera with a narrow band-pass filter at the aluminum line radiation wavelength. The LIBS plasma 52 from the ablated aluminum sample 50 with a light diameter on the order of 1 millimeter.

Figure 7B:
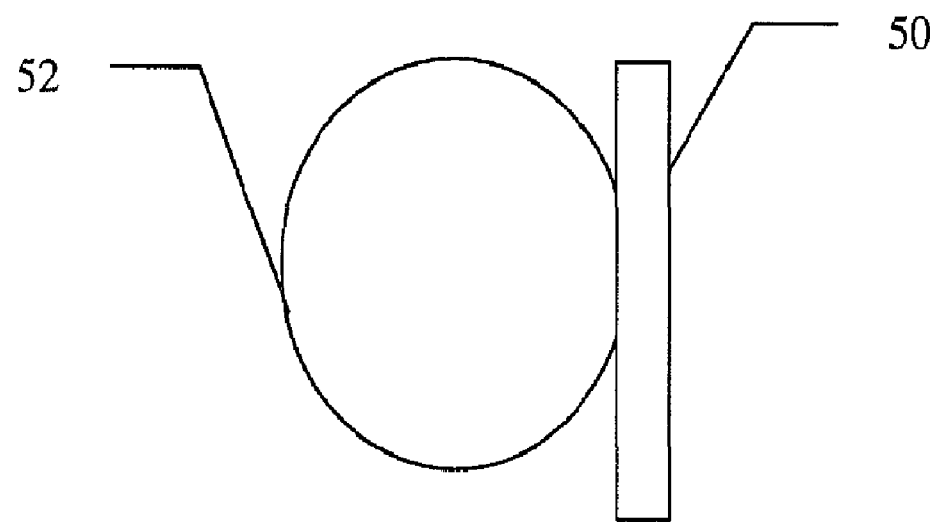
FIG. 7B is a schematic representation of an optical image of an aluminum line radiation light at 30 mJ laser energy for the LAMPS technique.

FIG. 7B is a schematic representation of an optical image of an aluminum line radiation light at 30 mJ laser energy for the LAMPS technique using a 1 millisecond microwave pulse of 600 Watts. The plasma 52 has grown to a size on the order of 5 millimeters diameter and 10 millimeters in length. With the LAMPS plasma size and duration matched to the ablated sample plume its signal strength is vastly greater than the LIBS signal. With 3 millisecond microwave pulses the plasma grows to centimeter scales.

These experiments have realized additional beneficial characteristics for LAMPS over the standard LIBS technique. LAMPS reduces the variation in spectral signal compared to LIES because the LIES laser has large shot-to-shot variation (~10-50%) compared to the 1% power variation of microwave sources. The light collected from an aluminum sample varies only 2% over many measurements of the LAMPS signal. This characteristic makes LAMPS capable of quantitative analysis, whereas LIES is not. Furthermore, LIBS plasmas are too dense during their first 1-2 microseconds that they require spectral data collection to be triggered after this time to avoid the large spectral continuum and to sample the line radiation. Alternately, the LAMPS plasma has strong line radiation and little spectral continuum. This avoids the need for sophisticated triggering to delay data collection after the first few microseconds of the ablation laser pulse. Furthermore, sequencing the microwave pulse with the ablation laser pulse is not critical and the microwaves can be routinely pulsed before the LIBS laser pulse. Consequently, the ablation laser energy is substantial smaller (0.001-30 mJ) for the LAMPS technique compared to the 200 mJ laser energy used in LIBS to create a useful signal. The large LIBS laser energy routinely damages samples. All of these characteristics make Lamps an attractive quantitative analysis technique.

Figure 8:
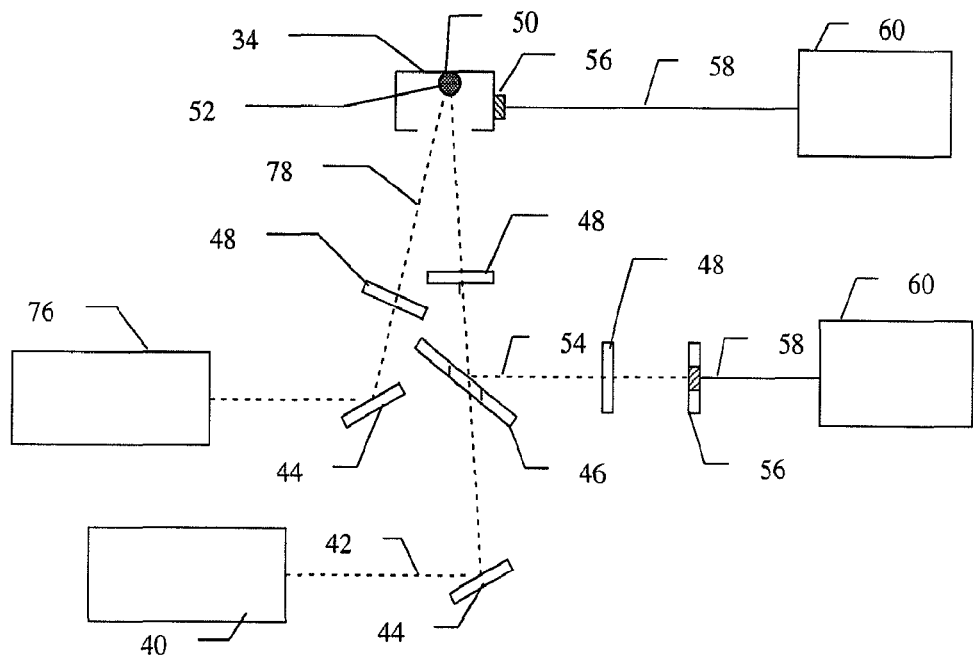
FIG. 8 is the experimental configuration including the layout of the optical system, plasma sustained laser, and target chamber.

FIG. 8 is the experimental configuration including the layout of the optical system, plasma sustained laser, and target chamber. In this alternate embodiment of LAMPS, the plasma 52 is sustained with a second laser 76 instead of with the microwave generator 36. The second laser 76 may, for instance, be a $CO_2$ laser. The ablation laser 40 has pulse duration matched to the ablated sample plume. This is typically on the order of 1-5 milliseconds. The plasma 52 is produced in the usual way. The ablation laser 40 generates laser light 42. The laser light 42 reflects off the mirror 44 and passes through a hole in the large mirror 46 and is focused with the lens 48 onto the sample 50. When the ablation laser 40 is fired, the laser light 42 ablates material to be analyzed from the sample 50. The $CO_2$ second laser 76 creates the plasma 52. The light 54 from the plasma 52 is collected by the large mirror 46 and is then focused with the lens 48 onto the optical fiber 58 that is held in place with the fiber mount 56. The optical fiber 58 transports the light 54 of the plasma 52 to a spectrometer 60 to analyze the plasma light 54. There can be an additional optical fiber 58 viewing the plasma 52 from the side and with its fiber mount 56 attached directly to the microwave cavity 34. The second laser 76, also known as the heating laser, reflects off the mirror 44, and is focused by the lens 48 onto the plasma 52 created in the microwave cavity 34 that acts as a sample chamber. The heating laser light 78 is synchronized to the firing of the ablation laser 40. The range of useable heating laser wavelengths includes 10-0.01 microns.

The second laser 76 may, for instance, be a k-500 $CO_2$ laser supplied by Coherent, Inc. of Santa Clara, Calif.

Figure 9:
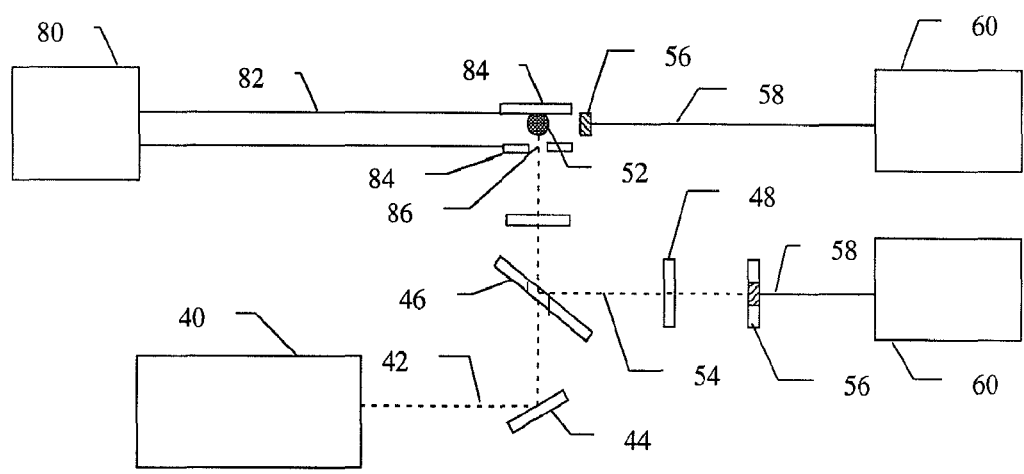
FIG. 9 is the experimental configuration including the layout of the optical system, high voltage power supply system, and high voltage electrodes.

FIG. 9 is the experimental configuration including the layout of the optical system, high voltage power supply system, and high voltage electrodes. Another alternate technique to LAMPS is to sustain the plasma 52 with a high voltage power supply 80. The pulse length of the high voltage power supply 80 is on the order of 0.5-5 milliseconds. The high voltage power supply 80 is connected to two high voltage electrodes 84 with high voltage wires 82. The plasma 52 is produced in the usual way. The ablation laser 40 generates laser light 42. The laser light 42 reflects off the mirror 44 and passes through a hole in the large mirror 46 and is focused with the lens 48 through a hole 86 in one of the two high voltage electrodes 84, where the sample 50 to be analyzed is mounted. When the ablation laser 40 is fired, the laser light 42 ablates material to be analyzed from the sample 50. The plasma 52 is created between the two high voltage electrodes 84. The light 54 from the plasma 52 is collected by the large mirror 46 and is then focused with the lens 48 onto the optical fiber 58 that is held in place with the fiber mount 56. The optical fiber 58 transports the light 54 of the plasma 52 to the spectrometer 60 to analyze the plasma light 54. There can be an additional optical fiber 58 viewing the plasma 52 from the side and with its fiber mount 56 attached directly to the two high voltage electrodes 84.

The high voltage power supply 80 may, for instance, be a model EH10R10 power supply supplied by Glassman High Voltage, Inc. of High Bridge, N.J.

Figure 10:
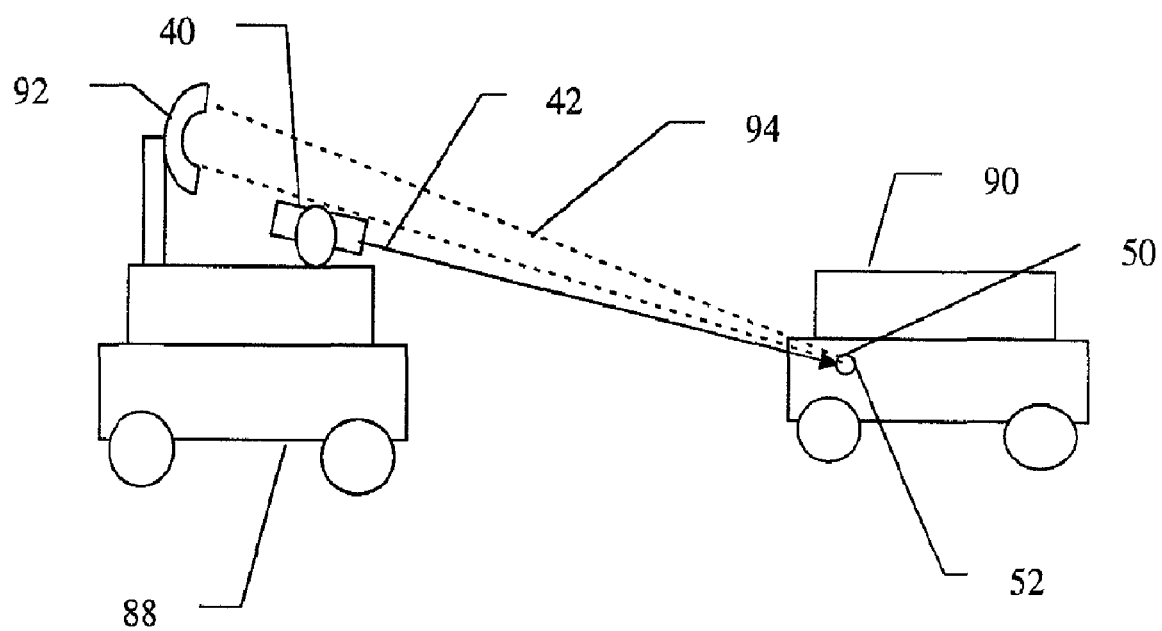
FIG. 10 is a schematic diagram of a vehicle mounted LAMPS system.

FIG. 10 is a schematic diagram of a vehicle mounted LAMPS system illustrating the concept of LAMPS at a distance with the ablation laser 40 and a microwave dish or antenna 92 mounted in a carrier vehicle 88, that may, for instance, be a Humvee. The microwave dish or antenna 92 focuses a microwave beam 94 to a spot some distance from the carrier vehicle 88. The laser light 42 and the microwave beam 94 are focused together to the same spot in space or on a surface that is the sample 50 to be analyzed. Here the laser light 42 and the microwave beam 94 are focused to the surface of a target vehicle 90. The ablation laser 40 creates the sample plume and the microwave beam 94 make the sample 50 to the size of the sample plume. The LAMPS technique can be greater than the LIBS technique by a factor of a 1000.

Such a vehicle mounted microwave beam has, for instance, been developed by the Joint Non-Lethal Weapons Program of the US Department of Defense. Termed an Active Denial System, the vehicle mounted microwave beam has been integrated by Raytheon Corp, in Boston Mass., using a high powered, 95 GHz gyrotron microwave tube supplied by CPI, Inc. in Palo Alto, Calif.

An alternate approach to the LAMPS technique at a distance is to substitute the microwave generator 36 and microwave dish or antenna 92 with a second laser 76 to sustain the plasma 52. The ablation laser 40 and the second laser 76 are focused together to the same spot in space or on a surface that is the sample 50 to be analyzed. The ablation laser 40 creates the sample plume and the additional laser 76 make the plasma 52 match the sample plume resulting in more signal than would be created by a standard LIBS technique. Signals can be larger than a 1000 fold.

One of ordinary skill in the electronics art will realize that their may be other energy sources that could be used to prolong the plasma such as, but not limited to, a radio frequency power energy source that may, for instance, be in the radio frequency range of 1-100 MHz.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

INDUSTRIAL APPLICABILITY

In the field of trace element analysis there is significant interest in a more sensitive, less damaging system such as the LAMPS technology of this invention. Such a sensitive, trance element analysis system would be of considerable utility as, for instance, a way to remotely and non-damagingly detect explosive residue on car door panels. Such a technique would also be useful in characterizing gemstones, including diamonds.

What is Claimed:

1. A spectroscopic method, comprising:
    directing laser energy to a sample material for a first period of time, thereby igniting a plasma containing said sample material;
    supplying energy from a second energy source to said plasma, while said plasma remains ignited, for a second period of time, said second period of time being longer than said first period of time, thereby maintaining radiation emission by said plasma; and
    detecting said radiation emitted from said plasma.

2. The method of claim 1 wherein directing said laser energy to said sample material further comprises ablating said sample material.

3. The method of claim 1 wherein directing said laser energy to said sample material further comprises vaporizing said sample material.

4. The method of claim 1 wherein said radiation emission maintained by said second energy source is characteristic radiation that is characteristic of an atomic composition of one or more elements in said sample material.

5. The method of claim 1 further comprising identifying one or more chemical elements or compounds contained in said sample material.

6. The method of claim 1 wherein said second energy source comprises a microwave energy source.

7. The method of claim 1 wherein said second energy source comprises a second laser source.

8. The method of claim 1 wherein detecting said emitted radiation comprises providing a spectrometer.

9. The method of claim 1 wherein said laser energy is up to 50 milli Joules.

10. The method of claim 6 wherein said microwave energy source comprises a power of up to 10 kW and a frequency up to 300 GHz.

11. The method of claim 7 wherein said second laser source has a power up to 5000 Watts.

12. The method of claim 1 wherein said second period of time is at least twice as long as said first period of time.

13. The method of claim 1 wherein said second period of time is at least 50 times as long as said first period of time.

14. A spectroscopic device, comprising:
    a sample chamber comprising a sample material exposed to a laser beam for a first period of time such that a plasma containing said sample material is ignited;
    a second energy source energizingly linked to said plasma, while said plasma remains ignited, for a second period of time, said second period of time being longer than said first period of time, thereby maintaining radiation emission by said plasma; and
    a radiation detector receiving said radiation emission from said plasma.

15. The device of claim 14 wherein exposing said sample material to said laser further ablates said sample material.

16. The device of claim 14 wherein exposing said sample material to said laser further vaporizes said sample material.

17. The device of claim 14 wherein said radiation emission maintained by said second energy source is characteristic radiation that is characteristic of an atomic composition of one or more elements in said sample material and further comprising identifying one or more chemical elements or compounds contained in said sample material.

18. The device of claim 14 wherein said second energy source comprises a microwave energy source and said radiation detector comprises a spectrometer.

19. The device of claim 14 wherein said second energy source comprises a second laser source and said radiation detector comprises a spectrometer.

20. The device of claim 14 wherein said second period of time is at least 50 times as long as said first period of time.

21. A spectroscopic apparatus, comprising:
    laser means for igniting a plasma containing a sample material by applying laser energy for a first period of time;
    second energy source means for maintaining radiation emission by said plasma by applying energy to said plasma for a second period of time, said second period of time being longer than said first period of time, and capable of being energizingly linked to said plasma while it remains ignited; and
    detection means for observing said radiation emitted from said plasma.

22. The apparatus of claim 21 wherein said laser means further ablates said sample material.

23. The apparatus of claim 21 further comprising identification means for identifying one or more chemical elements or compounds contained in said sample material.

* * * * *